United States Patent [19]

Nagamochi et al.

[11] Patent Number: 5,365,313
[45] Date of Patent: Nov. 15, 1994

[54] IMAGE FORMING APPARATUS FOR CONTROLLING IMAGE DENSITY USING LOGARITHM COMPRESSING MEANS

[75] Inventors: Katsuya Nagamochi, Tokyo; Rintaro Nakane, Yokohama, both of Japan

[73] Assignee: Kabushiki Kaisha Toshiba, Kawasaki, Japan

[21] Appl. No.: 32,299

[22] Filed: Mar. 17, 1993

[30] Foreign Application Priority Data

Sep. 24, 1992 [JP] Japan ................... 4-255081

[51] Int. Cl.⁵ ........................................... G03G 15/00
[52] U.S. Cl. ................................... 355/208; 355/246; 250/214 L; 356/445; 327/350; 327/362
[58] Field of Search ................ 355/208, 246; 118/665; 307/491, 492, 310; 250/214 L; 356/445

[56] References Cited

U.S. PATENT DOCUMENTS

| | | | |
|---|---|---|---|
| 3,992,622 | 11/1976 | Numata et al. | 307/491 X |
| 4,096,382 | 6/1978 | Numata et al. | 307/310 X |
| 4,277,162 | 7/1981 | Kasahara et al. | 355/14 R |
| 4,313,671 | 2/1982 | Kuru | 355/246 X |
| 4,318,610 | 3/1982 | Grace | 355/14 D |
| 4,750,838 | 6/1988 | De Wolf et al. | 356/445 |
| 4,801,980 | 1/1989 | Arai et al. | 355/246 X |
| 4,870,460 | 9/1989 | Harada et al. | 355/246 |
| 4,975,747 | 12/1990 | Higuchi | 355/246 |
| 5,083,160 | 1/1992 | Suzuki et al. | 355/208 |
| 5,099,279 | 3/1992 | Shimizu | 355/208 |
| 5,107,302 | 4/1992 | Bisaiji | 355/246 |
| 5,208,655 | 5/1993 | Cox et al. | 356/445 |

*Primary Examiner*—Joan H. Pendegrass
*Attorney, Agent, or Firm*—Foley & Lardner

[57] ABSTRACT

A toner depositing amount measuring apparatus for measuring the amount of toner deposited on a photosensitive drum includes a light source for irradiating the surface of the photosensitive drum with light and a photoelectric converting section for receiving the reflected light and converting the received reflected light into an electric signal. A logarithmic calculation is applied to the output signal of the photoelectric converting section in a logarithm-compressing section. The temperature characteristics of the logarithm-compressing section are compensated for in a temperature compensating section. The amount of the toner deposition is calculated in a toner depositing amount calculating section based on a difference between the data during non-deposition of the toner and the data during deposition of the toner, the data being obtained from the logarithm-compressing section. Further, image forming conditions are changed in a control section in accordance with an output signal denoting the calculated deposition amount of the toner so as to control the density of the image formed.

15 Claims, 10 Drawing Sheets

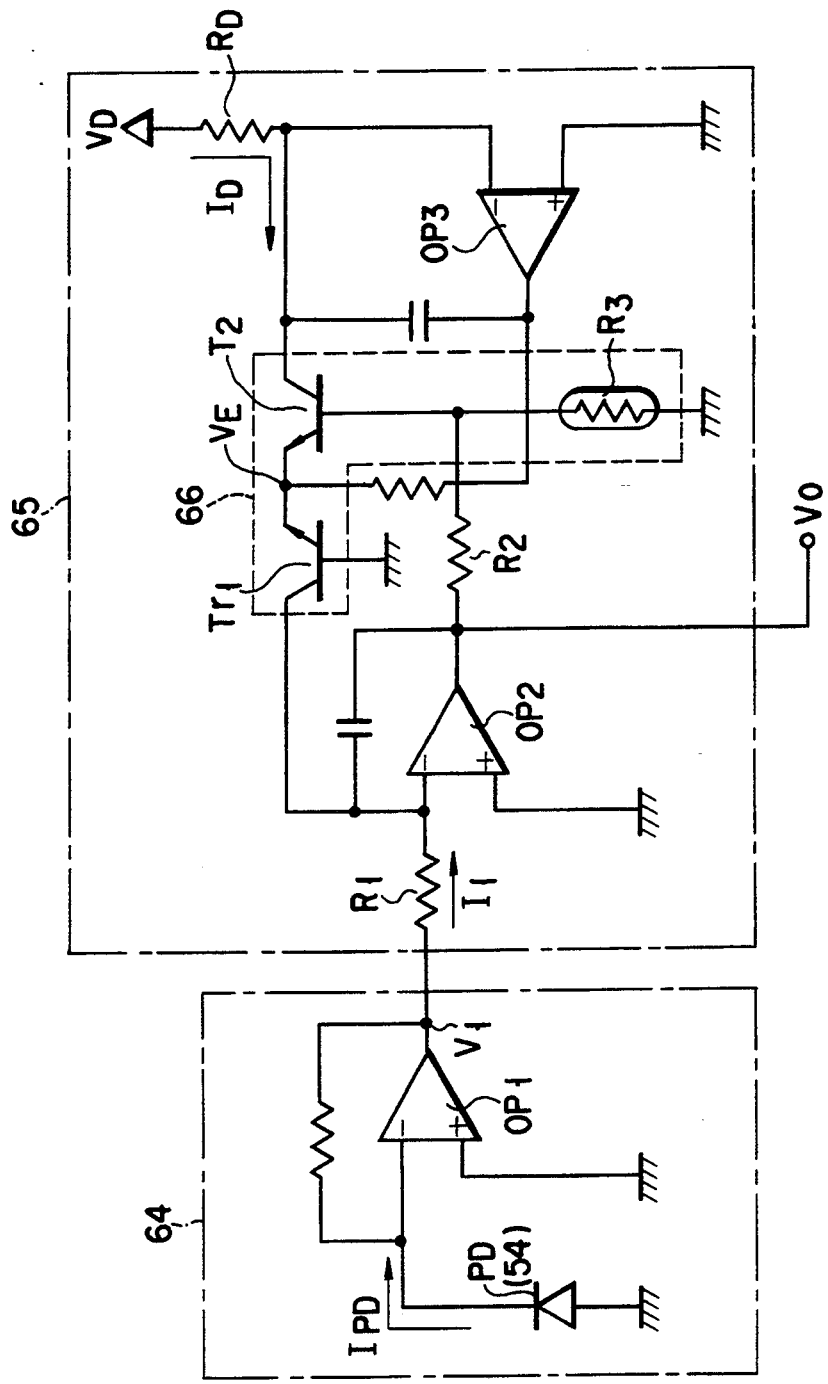
F I G 5

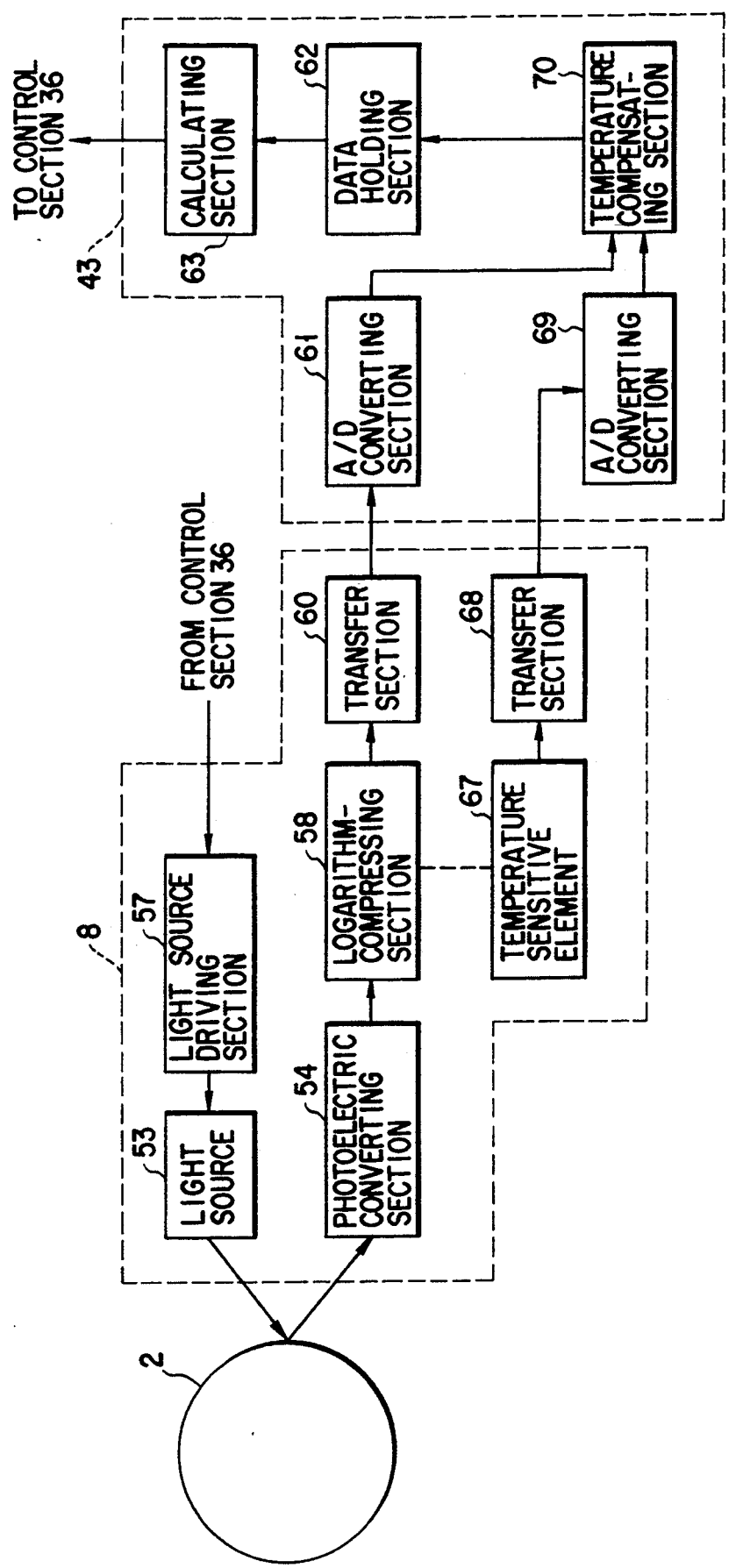
F I G. 7

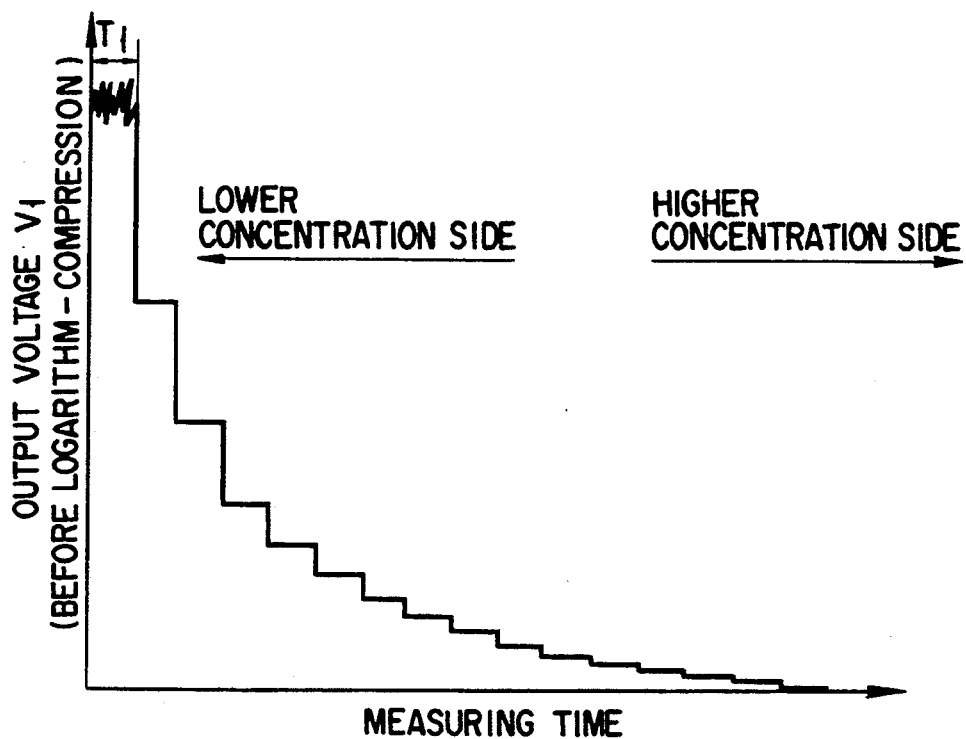
F I G. 10
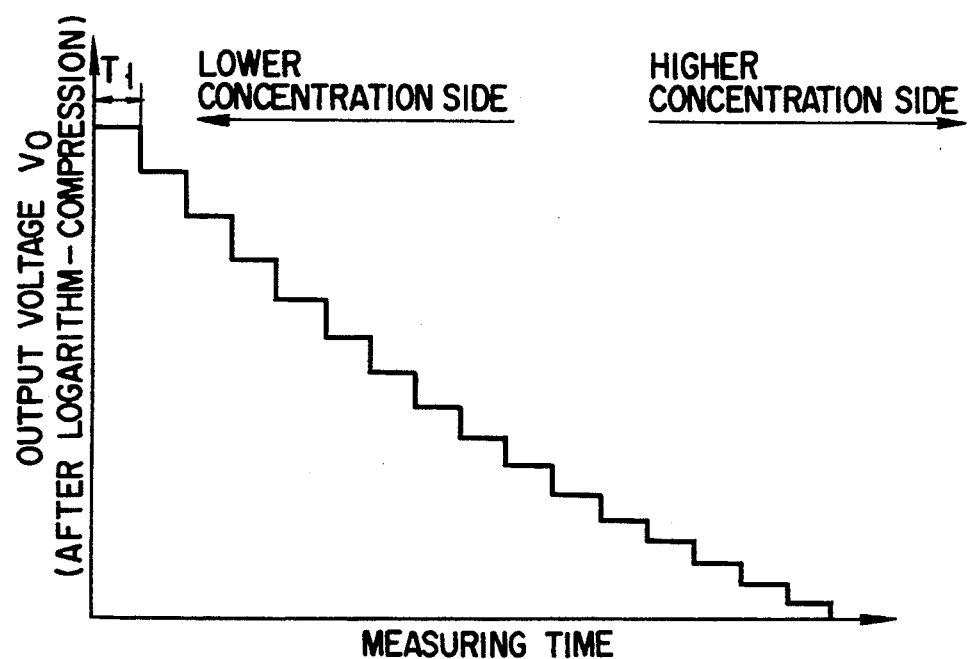
F I G. 11

IMAGE FORMING APPARATUS FOR CONTROLLING IMAGE DENSITY USING LOGARITHM COMPRESSING MEANS

BACKGROUND OF THE INVENTION

1. Field of the Invention

The present invention relates generally to an image forming apparatus and, more particularly, to an electrophotographic image forming apparatus, such as a color laser printer or a color digital copier.

2. Description of the Related Art

In an image forming apparatus, such as an electrophotographic color digital copier or color laser printer, the image density of the printed material or copied material is changed in some cases depending on a change in the environmental conditions or lapse of time. In a multigradation type printer or digital copier, as well as an analog copier, it is important to suppress changes in image density so as to stabilize the image density of the printed or copied material.

In a conventional image forming apparatus, some tolerance is imparted to the material forming the apparatus itself and to the image forming process itself such that the image density of the printed material or copied material can be stabilized by a maintenance operation. With the conventional technique, however, the tolerance imparted to the material and the image forming process itself has its own limit. Also, maintenance is laborious and costly. In addition, the period of change in the image density of the printed material or copied material is shorter than the frequency of maintenance. It follows that it is impossible to obtain a stable image density of the printed material or copied material by maintenance alone.

Recently, a new technique is being proposed for correcting the change in the image density, which is caused by the change in the environmental condition or by the lapse of time, in an interval shorter than that of normal maintenance operations. In the new technique, the amount of developing agent (toner) attached to an image carrier (photosensitive drum) included in an image forming apparatus is measured by a toner measuring means using an optical element such as a photo sensor. The measured value is compared with a reference value covering the case where a toner is not attached to the image carrier. Based on the result of the comparison, the image forming conditions, such as the charging amount of the image carrier, developing bias voltage, light-exposure amount, and toner concentration, are changed to keep constant the amount of the toner attached to the image carrier. The image forming apparatus employing the particular technique makes it possible to obtain a stable image density all the time.

However, the apparatus employing the new technique described above leaves room for further improvement. In the new technique, it is necessary to measure the amount of light reflected from the image carrier itself. What should be noted is that the light reflection from the image carrier is not uniform, but changes periodically. Where measuring of the toner amount attached to the image carrier is affected by the nonuniform light reflection from the image carrier, it is certainly possible to offset the range of change caused by the nonuniform light reflection by the comparison noted above between the measured value and the reference value. However, the measuring of the toner amount attached to the image carrier is scarcely affected, in general, by the nonuniform light reflection from the image carrier in the case where the toner attached to the image carrier. It follows that the nonuniform light reflection from the image carrier itself is output as it is, leading to errors of measurement and making it impossible to measure accurately the toner amount attached to the image carrier.

What should also be noted is that, where an image forming apparatus is enabled to perform a certain number of gradations, the values measured by the toner amount measuring means tend to have a narrow detection range in the high density stage and a broad detection range in the low density stage. As a result, the accuracy of measurement is impaired, if a random reading appears in the stage of transferring the measured result.

An analog/digital (A/D) converter of high resolution is required for detecting an output signal having a narrow detection range in the high density stage and a broad detection range in the low density stage. However, a A/D converter of high resolution is costly, in general, leading to increased manufacturing costs for the entire image forming apparatus.

As described above, the conventional image forming apparatus is defective in that, in measuring the toner amount attached to the image carrier by using a toner amount measuring means, errors of measurement are caused by a nonuniform light reflection from the image carrier itself. Also, the accuracy of measurement is impaired by the mixing of a noise in the step of transferring a signal denoting the result of measurement. Further, there is a difference in the range of detection in respect of the light reflectivity of the toner. Under the circumstances, the conventional image forming apparatus is incapable of maintaining a stable image density.

SUMMARY OF THE INVENTION

It is, therefore, an object of the present invention to provide a new and improved image forming apparatus which permits suppressing the error of measurement caused by a nonuniform light reflection from an image carrier itself in the step of measuring the reflective light, prevents the accuracy of measurement from being impaired by the mixing of a noise in the step of transferring a signal denoting the result measurement, and also permits enlarging the dynamic range in respect of the light reflectivity of the toner, so as to maintain stable the image density.

According to one aspect of the present invention, there is provided an image forming apparatus, comprising:

means for forming an image on an image carrier, the image corresponding to image data to be formed with a developing agent under a predetermined image forming condition;

means for detecting the amount of said developing agent attached to the image carrier, the detecting means comprising:

a) means for directing a light beam toward a surface of the image carrier;

b) means for converting the light reflected from the surface of the image carrier into an electric signal;

c) means for logarithm-compressing the electric signal produced by the converting means; and d) means for calculating the amount of the developing agent in accordance with a logarithm-compressed output signal from said logarithm-compressing means, and means for setting the image forming condition in accordance with the amount of the developing agent detected by said detecting means so as to stabilize image density changes of the image formed on the image carrier.

Additional objects and advantages of the present invention will be set forth in the description which follows, and in part will be obvious from the description, or may be readily learned to practice of the present invention. The objects and advantages of the present invention may be realized and obtained by means of the features particularly pointed out in the appended claims.

BRIEF DESCRIPTION OF THE DRAWINGS

The accompanying drawings, which are incorporated in and constitute part of the specification, illustrate presently preferred embodiments of the present invention and, together with the general description given above and the detailed description of the preferred embodiments given below, serve to explain the principles of the present invention, in which:

FIG. 5 shows the construction of a specific circuit in a logarithm-compressing section;

FIG. 7 schematically shows the construction of an apparatus for measuring the toner depositing amount according to a second embodiment of the present invention;

FIGS. 10 and 11 collectively show the effect produced by the logarithm compression employed in the present invention, in which FIG. 10 shows the output voltage before the logarithm compression and FIG. 11 shows the output voltage after logarithm compression.

DETAILED DESCRIPTION OF THE PREFERRED EMBODIMENTS

Figure 1:
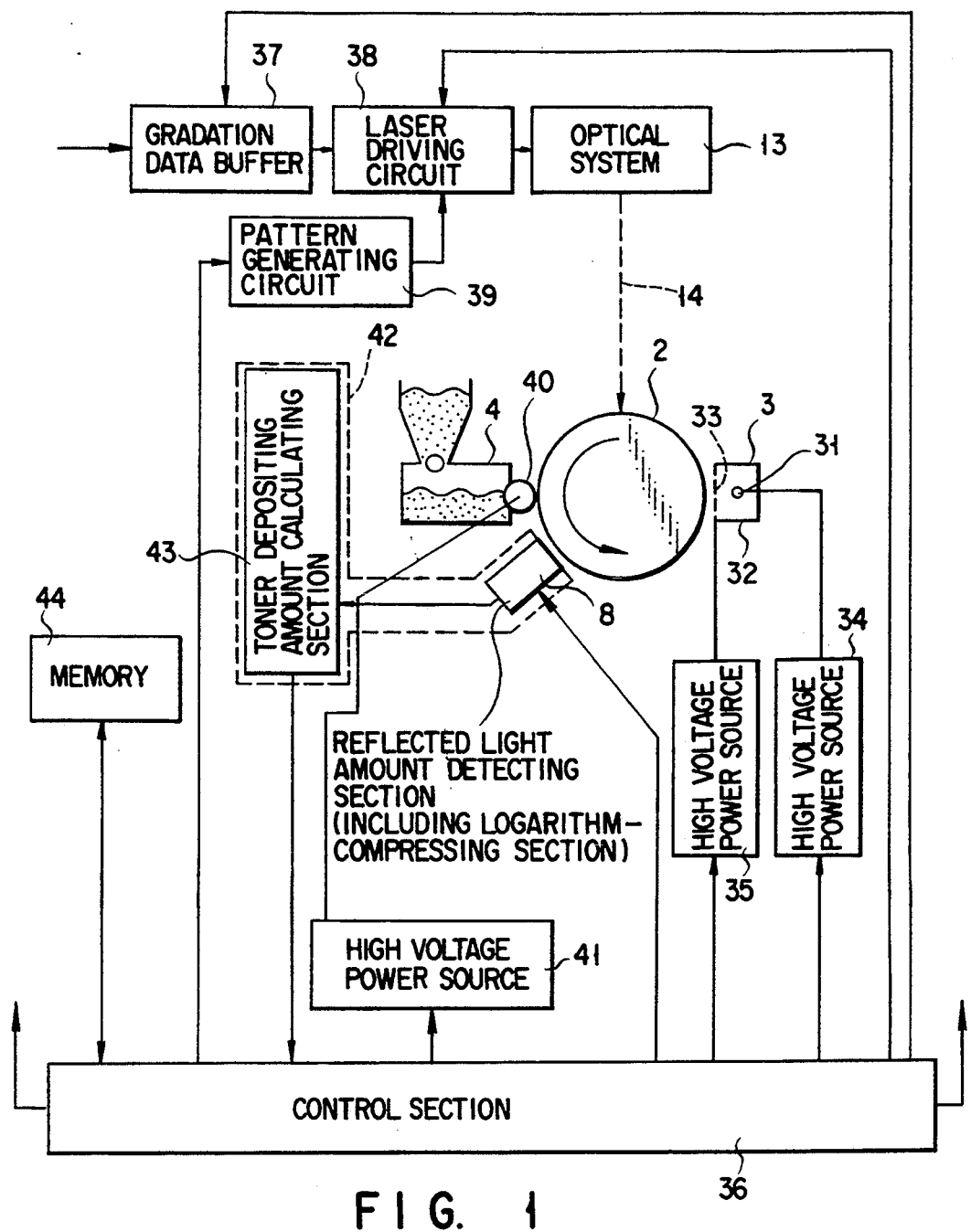
FIG. 1 is a block diagram schematically showing a color laser printer according to one embodiment of the present invention, the printer including a charging means, a light-exposing means, a developing means, and a control means thereof.

Reference will now be made in detail to the presently preferred embodiments of the present invention as illustrated in the accompanying drawings, in which like reference characters designate like or corresponding parts throughout the several drawings.

Figure 2:
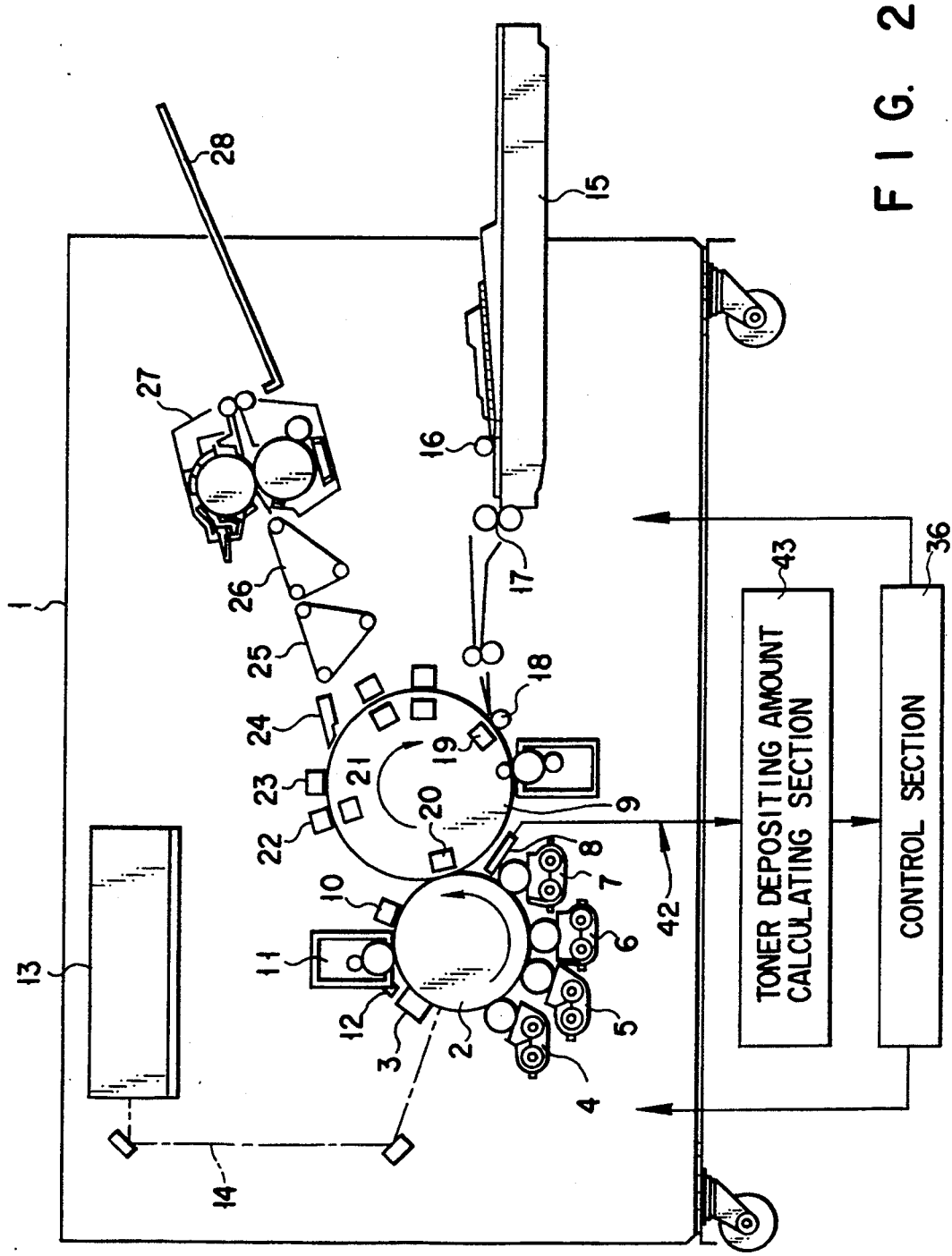
FIG. 2 schematically shows the construction of the color laser printer shown in FIG. 1.

FIG. 2 schematically shows the construction of a color laser printer as an example of an image forming apparatus of the present invention. As shown in FIG. 2, a photosensitive drum 2 rotating in a counterclockwise direction, which acts as an image carrier, is disposed in or near the central interior portion of a casing 1. Arranged around the photosensitive drum 2 are a charger 3 acting as a charging means, a developing means including a first developer 4, a second developer 5, a third developer 6, and a fourth developer 7, a reflected light amount detecting section 8, a transfer drum 9 acting as a supporting member of a transferred material, a charge eliminating device 10 before the cleaning step, a cleaner 11, and a charge eliminating lamp 12. The reflected light amount detecting section 8 comprises a logarithm-compressing portion connected to a toner depositing amount calculating section 43 to from a toner depositing amount measuring apparatus 42 which will described hereinafter in detail. Further, a control section 36 is connected to the toner depositing amount calculating section 43 for controlling the entire color laser printer.

The photosensitive drum 2 is rotated in a direction denoted by an arrow in FIG. 2, with the result that the surface of the drum 2 is uniformly charged by the charger 3. That region of the surface of the photosensitive drum 2 which is interposed between the charger 3 and the first developer 4 is exposed to a laser light beam 14 emitted from an optical system 13 acting as an exposing means. As a result, a latent image corresponding to the image data supplied to the optical system 13 is formed on the surface of the photosensitive drum 2.

The first to fourth developers 4 to 7 shown in FIG. 2 develop the latent image formed on the photosensitive drum 2 with toners of different colors. For example, the latent image is developed with a magnets toner in the first developer 4, with a cyan toner in the second developer 5, with a yellow toner in the third developer 6, and with a black toner in the fourth developer 7.

On the other hand, a transfer paper sheet (not shown), acting as a transfer material, is forwarded from a paper feeding cassette 15 by a paper feeder roll 16 toward the transfer drum 9. The transfer paper sheet is once aligned by a resist roller 17 and, then, forwarded by the resist roll to a predetermined position on the surface of the transfer drum 9. As a result, the transfer paper sheet is electrostatically held on the transfer drum 9 by a suction roll 18 and an electrostatic suction charger 19. The transfer paper sheet electro-statically held on the transfer drum 9 is transferred by the rotation of the transfer drum 9 in a clockwise direction as denoted by an arrow.

The developed toner image formed on the photosensitive drum 2 is transferred onto the transfer paper sheet by a transfer charger 20 in a contact region between the photosensitive drum 2 and the transfer drum 9. In printing a plurality of colors, a plurality of steps, each consisting of one complete rotation of the transfer drum 9, are carried out by switching the first to fourth developers 4 to 7 so as to transfer the toner images of a plurality of colors onto the transfer paper sheet.

The transfer paper sheet having the toner image transferred thereto is further transferred by the rotation of the transfer drum 9 so as to have its charge eliminated by a charge eliminating system consisting of an inner charge eliminating device 21 before separation, an outer charge eliminating device 22 before separation, and a charge eliminating device 23 for separation. Then, the transfer paper sheet is peeled off the transfer drum 9 by a separating claw 24 and is transferred of to a fixing device 27 by transfer belts 25 and 26. The toner on the transfer paper sheet is heated by the fixing device 27 so as to be melted and is fixed to the transfer paper sheet immediately after discharged from the fixing device 27. The transfer paper sheet having the toner image fixed thereto is discharged onto a takeup tray 28.

FIG. 1 is a block diagram schematically showing a color laser printer according to one embodiment of the present invention; the printer including a charging means, a light-exposing means, a developing means and a control means therefor. As shown in FIG. 1, the photosensitive drum 2 is rotated in a counterclockwise direction as denoted by an arrow. The charger 3 consists essentially of a charging wire 31, a conductive case 32 and a grid electrode 33. The charging wire 31 is connected to a high voltage power source 34 for a corona discharge, with the result that the surface of the photosensitive drum 2 is charged by a corona discharge. The grid electrode 33 is connected to a high voltage power source 35 for a grid bias, with the result that the charging amount on the surface of the photosensitive drum 2 is determined by the grid bias voltage. These high voltage power sources 34 and 35 are connected to the control section 36, with the result that the output voltages of these high voltage power sources are controlled by the control section 36.

The surface of the photosensitive drum 2, uniformly charged by the charger 3, is exposed to the laser beam 14 emitted from the optical system 13. The laser beam 14 modulates image date and, thus, a latent image corresponding to the visible image to be formed is formed on the surface to the photosensitive drum 2. Gradation data supplied from external equipment (not shown) or a controller is stored in a gradation data buffer 37. The gradation characteristics of the printer are corrected in the gradation data buffer 37, so as to achieve conversion into data denoting the laser exposing time (or pulse width).

A laser driving circuit 38 is controlled by the control section 36, so as to be in synchronism with the scanning position of the laser beam 14. The laser driving power source (light emitting time) is modulated in accordance with data on the laser beam exposure time generated from the gradation data buffer 37. A semiconductor laser oscillator (not shown) included in the optical system 13 is driven to the modulated laser driving current, with the result that the semiconductor laser oscillator performs its light-emitting operation in accordance with the data controlling the exposure time.

The laser driving circuit 38 also performs a comparison between the output of a monitoring light receiving element (not shown) within the optical system 13 and a reference value, so as to have the output light amount of the semiconductor laser oscillator controlled at a predetermined value by the driving current.

On the other hand, a pattern generating circuit 39 is connected to the control section 36. Under the control by the control section, the pattern generating circuit 39 generates gradation data for a test pattern for the printer itself and a pattern for measuring the amount of deposited toner. The gradation data thus generated is supplied to the laser driving circuit 38.

The switching from the data on the laser exposure time generated from the gradation data buffer 37 to the gradation data generated from the pattern generating circuit 39 for a pattern for measuring the depositing amount of the toner is carried out under the control of the control section 36. Data selected by the control section 36 is supplied to the laser driving circuit 38.

A developing roller 40 included in the first developer 4 is formed of an electrically conductive material and is connected to a high voltage power source 41 for a developing bias. Thus, the developing roller 40 is rotated with a developing bias applied thereto so as to permit a toner to attach to the latent image formed on the photosensitive drum 2. The developed toner image thus formed within an image forming region is supported and transferred by the transfer drum 9 shown in FIG. 2 and, then, is transferred onto the transfer paper sheet. The high voltage power source 41 is connected to the control section 36 such that the output voltage of the high voltage power source is controlled by the control section 36.

In synchronism with the timing, when the light exposure point on the surface of the photosensitive drum 2 is positioned in a non-image region, the control section 36 serves to switch the data supplied to the laser driving circuit 38 from the data on the laser beam-exposing time, which is generated from the gradation data buffer 37, to the gradation data generated from the pattern generating circuit 39, so as to expose the gradation pattern for measuring the toner depositing amount to light in the non-image region on the surface of the photosensitive drum 2. Further, in synchronism with the timing when that region on the surface of the photosensitive drum in which the gradation pattern is exposed to light so as to be developed is moved to face the reflected light amount detecting section 8, a toner depositing amount measuring apparatus 42 measures the deposited amount of the toner. The toner deposited amount measuring apparatus 42 comprises the reflected light amount detecting portion 8 provided with a logarithm-compressing portion and a toner depositing amount calculating section 43 serving to calculate the toner depositing amount based on the output signal generated from the reflected light amount measuring portion 8, as described herein later in detail.

The output signal generated from the toner depositing amount measuring apparatus 42 is supplied to the control section 36. The output signal (measured value) generated from the toner depositing amount measuring apparatus 42 is compared within the control section 36 with a reference value of the tone depositing amount measured and stored in advance in a memory 44. Based on the result of the comparison, the control section 36 permits changing at least one of the image forming conditions including, for example, the grid bias voltage of the charger 3, the developing bias voltage of the developer 4, the amount of light exposure performed by the optical system 13, the toner concentration of the developing agent, and the light emitting time for the area gradation.

Data including the reference value of the toner depositing amount noted above are stored in the memory 44, in which the stored contents can be rewritten, connected to the control section 36.

Various other functions are performed by the control section 36. For example, switching is performed by the control section between the gradation data supplied from an external equipment (not shown) or a controller and the gradation data for a test pattern for the printer itself or for a pattern for measuring the toner depositing amount. Also, the output signal from the toner depositing amount measuring apparatus 42 is received by the control section 36. Further, the control section 36 serves to control the output amounts of the high voltage power sources 34, 35 and 41, to determine the target value of the laser driving power source, to determine the target value of the toner concentration, to control the toner supply, and to correct the gradation data to conform with the gradation characteristics of the printer.

Figure 3:
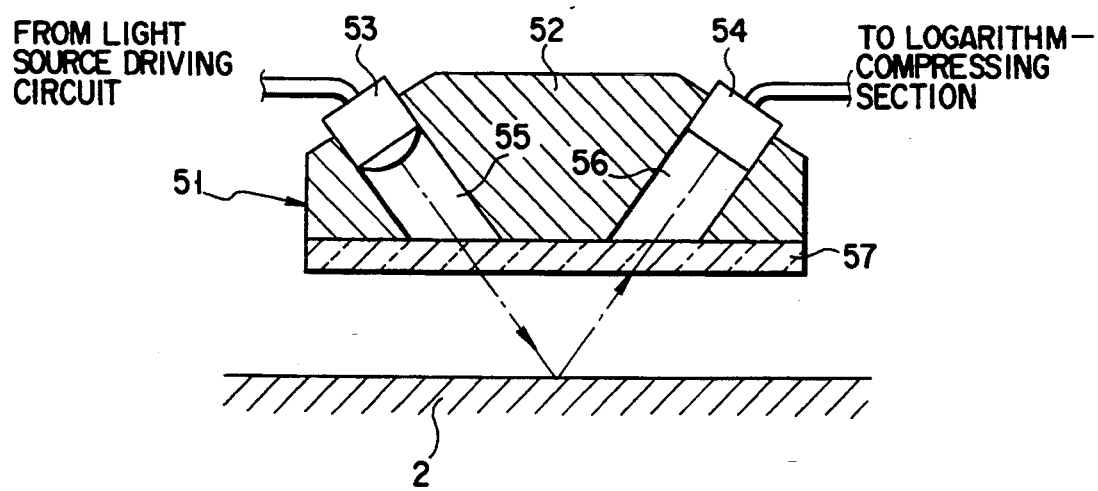
FIG. 3 is a cross sectional view schematically showing a detecting head portion of a reflected light amount detecting section.

FIG. 3 shows as an example a detecting head portion 51 of the reflected light amount detecting section 8 included in the toner depositing amount measuring apparatus 42. As shown in FIG. 3, the detecting head portion 51 comprises a supporting member 52 made of an insulating material. Formed in the supporting member 52 are a light source 53, a photoelectric converting section 54, an optical path 55 for guiding the light emitted from the light source 53 to the surface of the photosensitive drum 2, and an additional optical path 56 for guiding the light reflected from the surface of the photosensitive drum 2 to the photoelectric converting section 54. Further, the bottom surface of the supporting member 52, said bottom surface facing the surface of the photosensitive drum 2, is covered with a transparent plate 57.

The light emitted from the light source 53 runs through the optical path 5 to reach the surface of the photosensitive drum 2 and, then, is reflected by the surface of the photosensitive drum 2 or by the toner fixed after the developing stage. The reflected light runs through the optical path 56 to reach the photoelectric converting section 54, so as to be converted into an electric current corresponding to the amount of the reflected light and, then, the current is subjected to a current/voltage conversion.

Figure 4:
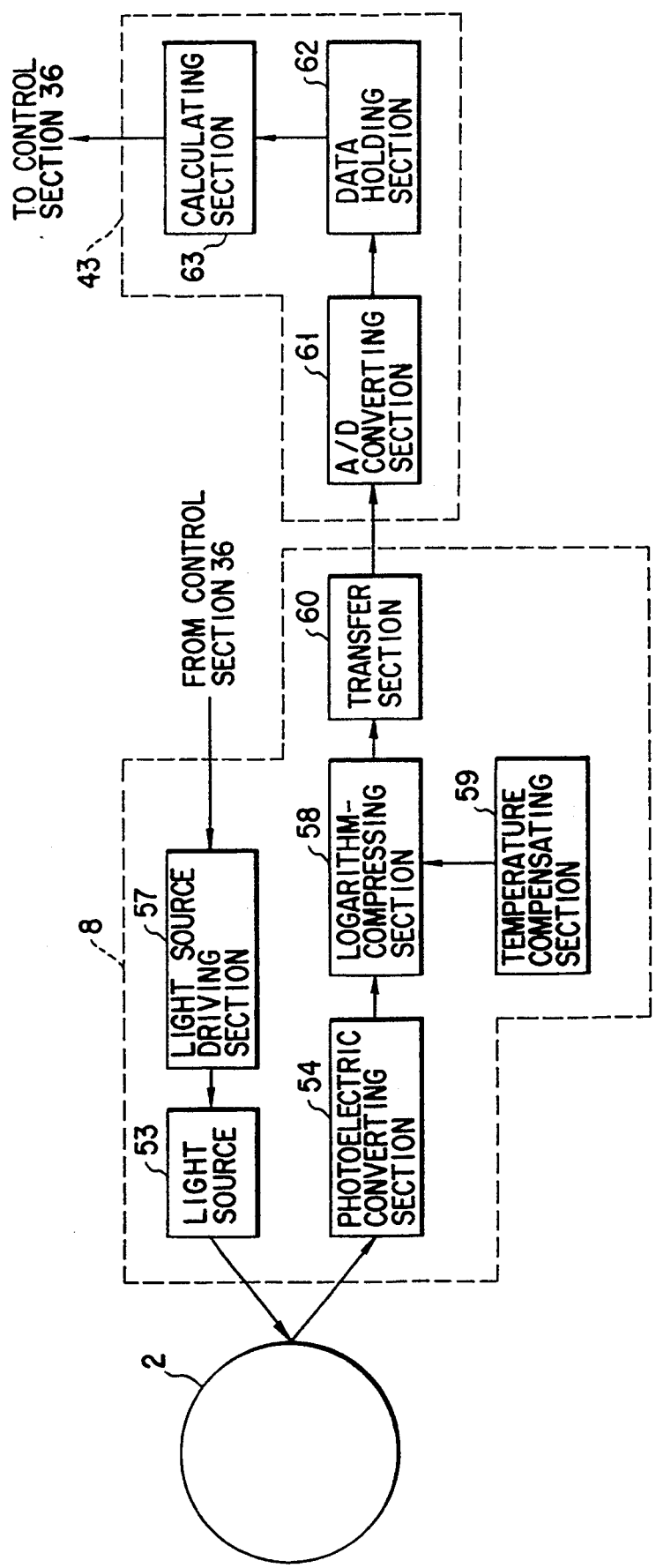
FIG. 4 shows the construction of an apparatus for measuring the deposited amount of a toner according to a first embodiment of the present invention.

FIG. 4 shows the construction of the toner depositing amount measuring apparatus 42 according to a first embodiment of the present invention. In this embodiment, a temperature compensating means is mounted in the reflected light amount detecting section 8. As described previously, the toner depositing amount measuring apparatus 42 can be roughly classified into the reflected light amount detecting section 8 and the toner depositing amount calculating section 43.

To be more specific, the reflected light amount detecting section 8 comprises the light source 53 serving to irradiate the surface of the photosensitive drum 2 with light emitted therefrom, a light source driving circuit 50 serving to control the driving of the light source 53 based on a control signal generated from the control section 36, the photoelectric converting section 54 which receives the light reflected from the photosensitive drum 2 and converts the received light into an electric signal, a logarithm-compression section 58 applies a logarithmic calculation to the electric signal generated from the photoelectric converting section. A temperature compensating section 59 provided with a temperature sensitive element (not shown) is electrically connected to the logarithm-compressing section 58 to perform compensation of the temperature characteristics of the logarithm-compressing section, and a transfer section 60 for transferring the output signal of the logarithm-compressing section to the toner depositing amount calculating section 43. Incidentally, the temperature sensitive element noted above is denoted as a member R3 in FIG. 5.

Where the output of the logarithm-compressing section 58 is dependent on temperature, the output of the logarithm-compressing section 58 tends to be changed greatly depending on the temperature characteristics of the logarithm-compression section 58. To overcome the difficulty, the temperature compensating section 59 compensates for the temperature characteristics of the logarithm-compressing section 58.

On the other hand, the toner depositing amount calculating section 43 serves to calculate the toner depositing amount on the basis of the signal supplied from the reflected light amount detecting section 8. As shown in FIG. 4, the toner depositing amount calculating section 43 comprises an A/D converting section 61, a data storing section (memory section) 62, and a calculating section 63. The signal supplied from the reflected light amount detecting section 8 is converted into a digital signal in the A/D converting section 61. The output signal on the surface of the photosensitive drum 2 during non-deposition of the toner and the output signal on the surface of the photosensitive drum 2 during deposition of the toner are stored in the data storing section 62.

Further the difference between the data collected during the toner deposition and the data collected during non-deposition of the toner, which are stored in the data storing section 62, is calculated in the calculating section 63. The result of the calculation performed in the calculating section 62 is transferred to the control section 36 as a measured value of the toner deposition, and is used for the image density control.

The toner depositing amount calculating section 43 can be provided singly as an exclusive circuit or, alternatively, can be mounted within the control section 36.

The toner depositing amount is calculated in the calculating section 63. Specifically, the light reflected from the surface of the photosensitive drum 2 is converted into a voltage in the photoelectric converting section 54, with a relationship of V=kP, where k denotes a coefficient, $P_{PC}$ represents the light reflected from the surface of the photo-sensitive drum 2 during non-deposition of the toner, and $P_{TN}$ represents the light reflected from the surface of the photosensitive drum 2 during deposition of the toner. It follows that the toner deposition amount Q can be calculated as follows:

$$Q = A \times \log V_{PC} - A \times \log V_{TN}$$
$$= A \times \log(P_{TN}/P_{PC})$$

where "$V_{PC}$" is the voltage converted from the light reflected from the surface of the photosensitive drum during non-deposition of the toner, "$V_{TN}$" is the voltage converted from the light reflected from the surface of the photosensitive drum during deposition of the toner, "Q" is the deposited amount of the toner, and "A" is a coefficient.

FIG. 5 shows as an example the electric circuit constituting the logarithm-compressing section 58. As shown in the drawing, the logarithm-compressing section 58 comprises a current-voltage converting section 64 and a logarithmic converting section 65. The current-voltage converting section 64 includes an operational amplifier OP1 and a photo diode PD acting as a photoelectric converting section 54. A current IPD, corresponding to the amount of the received light, is generated from the photo diode PD and, then, subjected to a current-voltage conversion in the operational amplifier OP1.

The output signal generated from the current-voltage converting section 64 is subjected to a logarithmic conversion in the logarithmic conversion section 65. As shown in FIG. 5, the logarithmic conversion section 65 comprises, for example, a temperature sensitive resistor element R3 acting as a temperature sensitive element and including a negative resistance element such as a thermistor, operational amplifiers OP2 and OP3, and NPN transistors Tr1 and Tr2 acting as a logarithm characteristic element.

An output voltage V1 generated from the current-voltage converting section 64 is converted into a current I1 by a resistor R1 included in the logarithmic converting section 65. The current in thus obtained acts as a collector current of the transistor Tr1 serving to perform the logarithmic conversion. On the other hand, a reference current ID, which is represented by a power source voltage VD for driving the circuit and a resistance RD, i.e., ID=VD/RD, is supplied to the collector of the transistor Tr2. The operating point of the transistor Tr2 is kept constant by the feedback function of the operational amplifier OP3. The common emitter voltage VE of the transistors Tr1 and Tr2 is represented as follows:

$$VE = -VBE1 \qquad (1)$$
$$= (kT/q) \times \ln(I1/IS)$$

where, "VE" is the common emitter voltage of the transistors Tr1 and Tr2, "IS" is the emitter saturation current (reference current) of the transistors Tr1 and Tr2, "VBE1" is the base-emitter voltage of the transistor Tr1, "k" is Boltzman constant, "T" is the absolute temperature, and "q" is charge of electron.

On the other hand, the base voltage VB2 of the transistor Tr2 is represented as follows:

$$VB2 = -VBE1 + VBE2 \qquad (2)$$
$$= (kT/q) \times \ln(ID/I1)$$

where, "VB2" is the base voltage or the transistor Tr2, and "VBE2" is the base-emitter voltage of the transistor Tr2.

It should be noted that the base voltage VD2 of the transistor Tr2 can be represented by dividing the output voltage VO after the logarithmic conversion by a resistor R2 and the temperature sensitive resistor element R3. It follows that the output voltage V0 after the logarithmic conversion can be represented as follows:

$$V0 = (R2 + R3)/R3 \times VB2 \qquad (3)$$
$$= (1 + R2/R3) \times kT/q \times \ln(ID/Ii)$$

The value of kT/q is 26 mV where the absolute temperature T is 300K (27° C.). The temperature characteristic in respect of a temperature change by 1° C. is about 1/300=0.3%. In order to compensate the temperature characteristic, a temperature sensitive resistor element having a temperature coefficient of 0.3%/° C. is used as the temperature sensitive resistor element R3. It should also be noted that, where the value of (1+R2/R3) is 16.7, i.e., (1+R2/R3)=16.7, formula (3) given above can be represented by a normal logarithm as follows:

$$\begin{aligned}VO &= (R2 + R3)/R3 \times VB2 \qquad (4)\\ &= (R2 + R3)/R3 \times 16.7 \times 0.026 \times \ln(ID/I1)\\ &= \log 10(ID/I1)\\ &= \log 10(ID \times R2/V1)\end{aligned}$$

Figure 6:
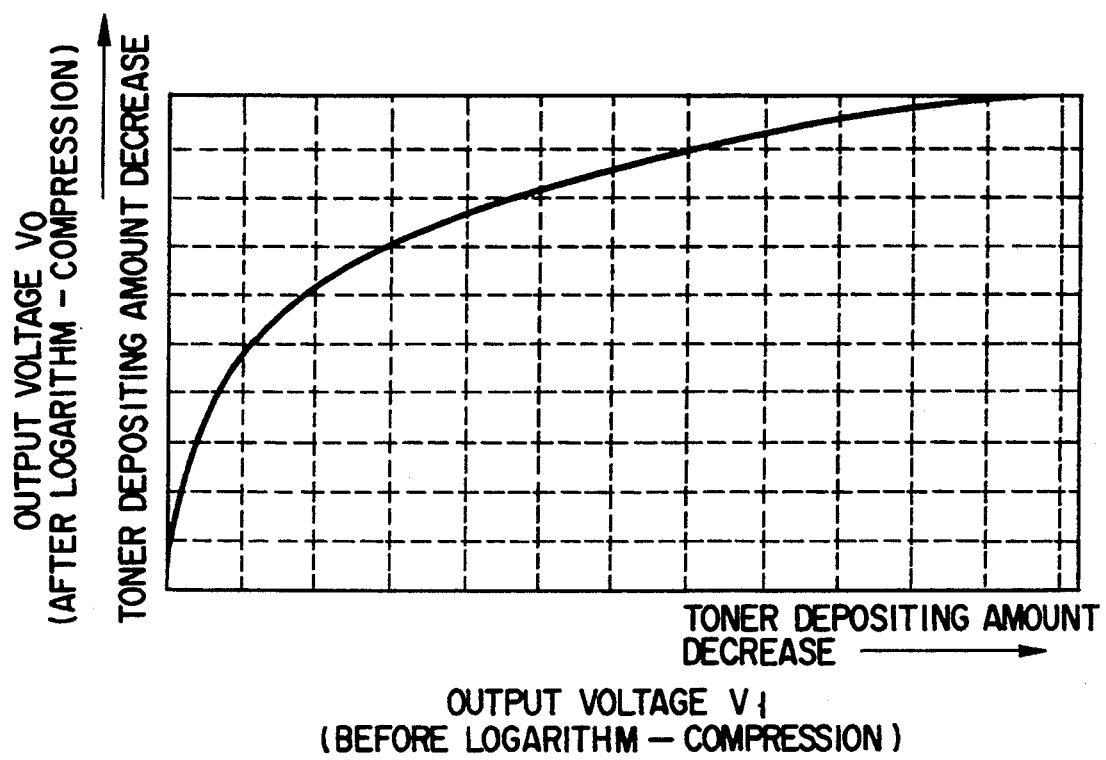
FIG. 6 is a graph showing the output voltage both before and after the logarithm compression.

FIG. 6 is a graph prepared by using formula (4) given above, i.e., a graph showing the relationship between the output voltage V1 of the current-voltage converting section 64, i.e., the output before the logarithm compression, and the output voltage V0 of the logarithm converting section 65, i.e., the output after the logarithm compression, with the coefficient (proportion gain) set at —A. The calculation formula in this case is as shown below:

$$V0 = -A \times \log 10(ID \times R2/V1) \qquad (5)$$

In the graph of FIG. 6, the output voltage V0 from the logarithm converting section 65 is plotted on the ordinate, with the output voltage V1 of the current-voltage converting section 64 being plotted on the abscissa. It should be noted that the toner deposition amount diminishes with increase in the output voltage V0 after the logarithm compression (upward direction of the ordinate). Also, the toner deposition amount is diminished with increase in the output voltage V1 before the logarithm compression (rightward direction of the abscissa). As seen from the graph, a range of a high concentration region in which the toner deposition amount is large can be broadened by performing the logarithm compression. It is also possible to diminish a range of a low concentration region in which the toner deposition amount is small by performing logarithm compression.

In the circuit shown in FIG. 5, a change in the temperature characteristics of transistors is detected by using a temperature sensitive element, i.e., the temperature sensitive resistor element R3. As shown in a region 66, denoted by a broken line in FIG. 5, the temperature sensitive resistor element R3 is arranged in the vicinity of and is electrically connected to the transistors Tr1 and Tr2 performing a logarithm conversion in a manner contradictory to the temperature characteristics of the logarithm-compressing section 58, with the result that the temperature compensation can be performed accurately.

In order to detect a change in temperature characteristics of the transistors Tr1 and Tr2 with high accuracy, it is desirable to seal the transistors Tr1, Tr2 and the temperature sensitive resistor element R3, which are positioned within the region 66 denoted by a broken line in FIG. 5, with a sealing member having a heat conductivity and insulating property so as to thermally connect and form an integral structure. An adhesive containing a silicone resin as a main component can be used as the sealing member. The integral structure thus prepared permits detecting a change in the temperature characteristics with a higher accuracy.

It should be noted that, in order to subject the detected amount of the toner deposition to an A/D conversion without employing a logarithm-compression as in the prior art, it is impossible to ensure a dynamic range, making it necessary to use an A/D converter of high resolution. However, if the logarithm-compressing section 58 is provided in the reflected light amount detection section 8 so as to perform a logarithm conversion before input of the A/D converter as in the present invention, a dynamic range can be ensured even if the resolution of the A/D converter is low. It follows that it is possible to use a cheap A/D converter of a low resolution, leading to a cost reduction.

FIG. 7 shows a toner depositing amount measuring apparatus 42 according to a second embodiment of the present invention. In this embodiment, temperature compensation can be achieved without electrically connecting a temperature sensitive element, i.e., the temperature sensitive resistor element R3, connected to the logarithm-compressing section 58. It should be noted that a temperature compensating means is mounted to the toner depositing amount calculating section 43 in this embodiment.

To be more specific, the reflected light amount detecting section 8 comprises the light source 53 for irradiating the surface of the photosensitive drum 2 with light, a light source driving circuit 57 serving to control the light source 53 in response to a control signal generated from the control section 36, the photoelectric converting section 54 which receives the light reflected from the surface of the photosensitive drum 2 for converting the received reflected light into an electric signal, a logarithm-compressing section 58 for subjecting the electric signal converted from the reflected light to a logarithmic calculation, a transfer section 60 for transferring the output signal of the logarithm-compressing section 58 to the toner depositing amount calculating section 43, a temperature sensitive element 67 such as a temperature sensitive resistor element serving to detect a change in the temperature characteristics of the logarithm-compressing section 58, and a transfer section 68 serving to transfer the output signal of the temperature sensitive element 67 to the toner depositing amount calculating section 43.

On the other hand, the toner depositing amount calculating section 43 comprises an A/D converting section 61 serving to convert the signal transferred from the transfer section 60 of the reflected light amount detection section 8 into a digital signal, another A/D converting section 69 serving to convert the signal transferred from the transfer section 68 of the reflected light amount detecting section 8 into a digital signal, a temperature compensating section 70, serving to compensate the temperature characteristics of the output signal generated from the A/D converting section 61, is response to the output signal of the A/D converting section 69, a data holding section (memory section) 62 serving to store the output signal generated from the temperature compensating section 70 in respect of the surface of the photosensitive drum 2 during non-deposition of the toner and the output signal generated from the temperature compensating section 70 in respect of the surface of the photosensitive drum 2 during deposition of the toner, and a calculating section 63 serving to calculate the difference between the data during non-deposition of the toner and the data during deposition of the toner, said data being held in the data holding section 62.

The result of the calculation performed in the calculating section 63 is supplied to the control section 36 as the measured amount of the deposited toner so as to perform various operations including the image density control.

Figure 8:
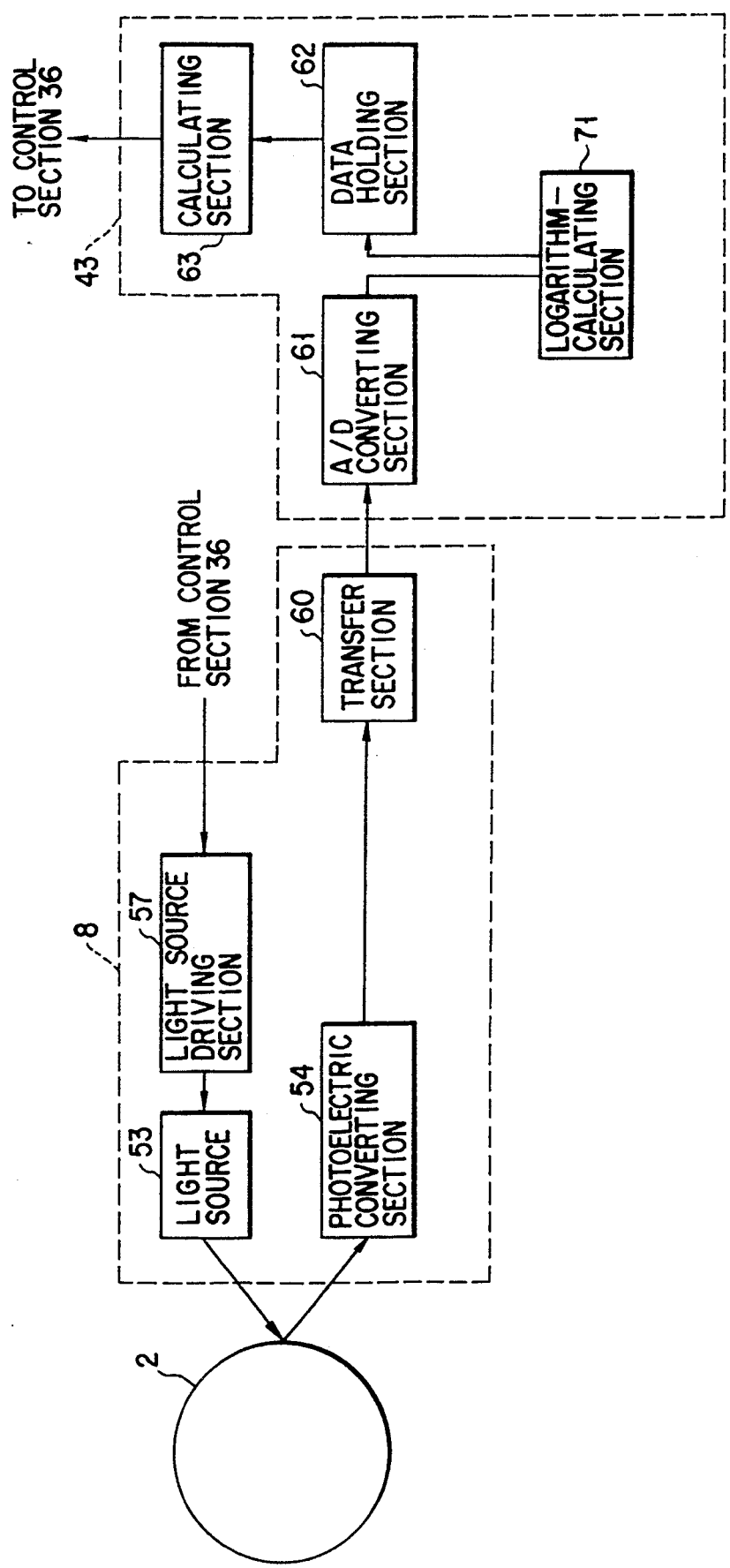
FIG. 8 schematically shows the construction of an apparatus for measuring the toner depositing amount according to a third embodiment of the present invention.

FIG. 8 shows a toner depositing amount measuring apparatus 42 according to a third embodiment or the present invention. In this embodiment, a logarithm conversion is performed within the toner depositing amount calculating section 43.

To be more specific, the reflected light amount detecting section 8 in this embodiment comprises the light source 53 serving to irradiate the surface of the photosensitive drum 2 with light, the light source driving circuit 57 serving to control the driving or the light source 53 in response to a control signal generated from the control section 36, the photoelectric conversion section 54 which receives the light reflected from the surface of the photosensitive drum 2 and converts the received reflected light into an electric signal, and a transfer section 60 serving to transfer the electric signal generated from the photoelectric conversion section 54 to the toner depositing amount calculating section 43.

On the other hand, the toner depositing amount calculating section 43 comprises an A/D converting section 61 for converting the signal transferred from the reflected light amount detecting section 8 into a digital signal, a logarithmic calculating section 71 for applying a logarithmic calculation treatment to the output signal generated from the A/D conversion section 61, a data holding section (memory section) 62 for storing the output signal generated from the logarithmic calculating section in respect of the surface of the photosensitive drum during non-deposition of the toner and the output signal generated from the logarithmic calculating section in respect of the surface of the photosensitive drum during deposition of the toner, and a calculating section 63 for calculating the difference between collected from data the toner deposition and the data collected during non-deposition of the toner, said data being held in the data holding section 62.

The result of the calculation performed in the calculating section 63 is supplied to the control section as the data denoting the measured amount of the toner deposition so as to perform various operations including the image density control.

The particular construction shown in FIG. 8 makes it unnecessary to use the logarithm-compressing section 58 and the temperature sensitive element 67 serving to detect the temperature characteristics of the logarithm-compressing section 58.

Figure 9:
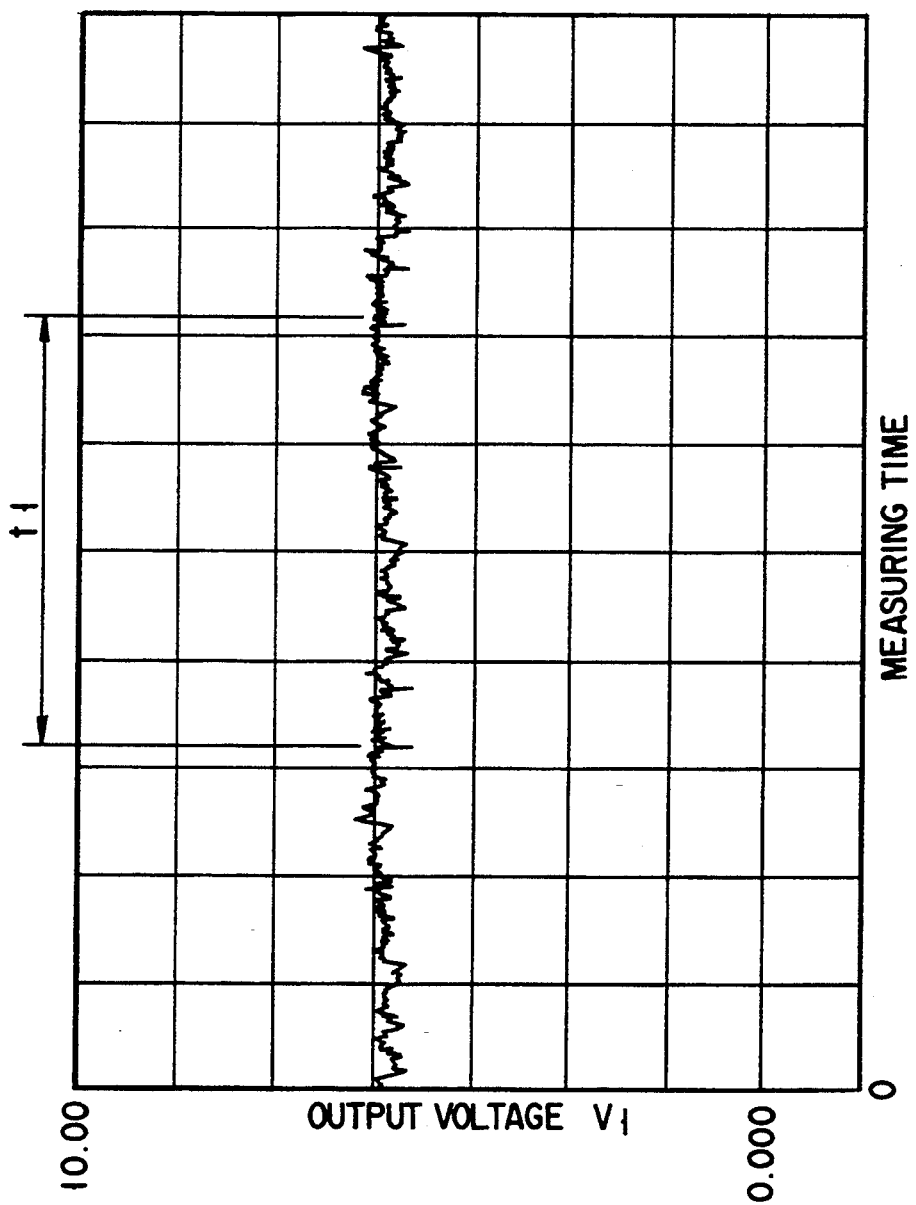
FIG. 9 is a graph showing the influence of a nonuniform light reflection from a photosensitive drum.

FIG. 9 shows the influence given by the non-uniform light reflection from the surface of the photosensitive drum 2. The graph of FIG. 9 denotes the changes with the measuring time in the output voltage V1 generated from the current-voltage converting section 64, i.e., the output which is generated when the light reflected from the surface of the photosensitive drum 2 is not subjected to a logarithm-compressing treatment in the case of measuring the reflected light from the surface of the photosensitive drum 2 to which is a toner is not deposited. The waveform shown in FIG. 9 represents the influence given by the nonuniform light reflection the surface of the photosensitive drum 2. It should be noted that the output signal is changed with a period t1. In a laser printer using a coherent light, a coating is applied to the surface of the photosensitive drum in order to avoid the image defect caused by an interference lattice stripe. The nonuniform coating or toughening treatment applied to the photosensitive drum cause the particular waveform shown in FIG. 9.

In the toner depositing amount calculating section 43, the toner depositing amount is determined on the basis of the difference between the output of the reflected light amount detecting section 8 during the toner deposition on the photosensitive drum 2 and the output of the reflected light amount detecting section 8 during non-deposition of the toner.

Incidentally, an appreciable difference is not brought about in the output of the reflected light amount detecting section 8 during the toner deposition. It follows that, if a difference between the two outout signals generated from the reflected light amount detecting section 8 is utilized in the toner depositing amount calculating section 43, the output from the toner depositing amount calculating section 43 is affected by the nonuniform light reflection from the photosensitive drum 2, resulting in failure to obtain an output signal accurately corresponding to the actual amount of the toner deposition.

FIG. 10 shows the output voltage V1 before the logarithm-compressing treatment, which is generated from the current-voltage converting section 64 and corresponds to the amount of the toner deposited on the surface of the photosensitive drum 2. On the other hand, FIG. 11 shows the output voltage vO after the logarithm-compressing treatment, which is generate from the logarithm converting section 65. As seen from these drawings, the logarithm compression employed in the present invention permits suppressing the adverse effect produced by the nonuniform light reflection from the surface of the photosensitive drum 2.

To be more specific, a section 1 shown in each of FIGS. 10 and 11 denotes the output owing to the reflected light from the surface of the photosensitive drum 2 itself. These drawings show that the toner deposition amount is increased with increase in the measuring time, i.e., toward right-hand region. What should be noted is that the nonuniform light reflection from the surface or the photosensitive drum 2 in a low concentration region in FIG. 10, which shows the output voltage V1 before the logarithm-compressing treatment, is made substantially linear in the changing portion after the logarithm-compressing treatment as shown in FIG. 11. It follows that the adverse effect given by the nonuniform light reflection can be diminished by the logarithm-compressing treatment employed in the present invention.

Concerning the reduction in the nonuniform light reflection from the photosensitive drum 2, the graph of FIG. 6 shows that a range is diminished in the low concentration region. This is because it is possible to diminish the width of change in respect of the change in the output signal such as the nonuniform light reflection from the photosensitive drum 2.

FIGS. 10 and 11 clearly show the effect produced by the logarithm compression applied to the output generated from the reflected light amount detecting section 8 in a high concentration region. As described previously, FIG. 10 shows the output voltage V1 generated from the current-voltage converting section 64, which is not subjected to a logarithm-compressing treatment, with FIG. 11 showing the output voltage V0 generated from the logarithm converting section 65 after application of the logarithm-compressing treatment. It is clearly shown in FIG. 10 that, in the low concentration region, a large difference is generated between two adjacent data in the level of the output voltage V1 generated from the current-voltage converting section 64 before application of the logarithm-compressing treatment. It is also shown that, in the high concentration region, a difference between two adjacent data in the level of the output voltage V1 is rendered substantially negligible.

On the other hand, the effect produced by the logarithm-compressing treatment can by clearly seen from FIG. 11. Specifically, a difference in the level of the output voltage V0 after the logarithm-compressing treatment is enlarged between two adjacent data in the high concentration region, compared with the data shown in FIG. 10, though the difference is diminished in the low concentration region in FIG. 11. In other words, the difference in the levels of the output voltage between two adjacent data in FIG. 11 is substantially equal to that in FIG. 10. It follows that the logarithm-compressing treatment employed in the present invention makes it possible to suppress the adverse effect given by the nonuniform light reflection from the photosensitive drum 2 and improve the dynamic range.

As described above in detail, the present invention provided an image forming apparatus which permits overcoming the defects inherent in the conventional apparatus. To reiterate, the present invention makes it possible to diminish the measuring error caused by the nonuniform light reflection from an image carrier and to enlarge the dynamic range with respect to the light reflecting characteristics of a developing agent. It follows that it is possible to suppress the deterioration in the measuring accuracy caused by the mixing or a noise in the step of transferring the signal denoting the result of measurement. Further, changes in the characteristics of the logarithm-compressing means, which are caused by a change in temperature, can be canceled in the present invention, so as to control the image density with a high accuracy, making it possible to maintain a high image quality.

Additional embodiments of the present invention will be apparent to those skilled in the art from consideration of the specification and practice of the present invention disclosed herein. It is intended that the specification and examples be considered as exemplary only, with the true scope of the present invention being defined by the claims which follow.

What is claimed is:

1. An image forming apparatus, comprising:
   means for forming an image on an image carrier, said image corresponding to image data to be formed with a developing agent under a predetermined image forming condition;
   means for detecting the amount of said developing agent attached to the image carrier, said detecting means comprising:
   a) means for directing a light beam toward a surface of the image carrier;
   b) means for converting the light reflected from the surface of the image carrier into an electric signal;
   c) means for logarithm-compressing the electric signal produced by said converting means; and
   d) means for calculating the amount of said developing agent in accordance with a logarithm-compressed output signal from said logarithm-compressing means,
   means for setting said image forming condition in accordance with the amount of the developing agent detected by said detecting means, so as to stabilize image density changes of the image formed on said image carrier; and
   means for compensating for the temperature characteristics of said logarithm-compressing means, said compensating means having a temperature sensitive element electrically responsive to the ambient temperature, said compensating means further including a temperature compensating section to compensate for the temperature characteristics of said logarithm-compressing means in accordance with the output signal generated by said temperature sensitive element, said temperature sensitive element not being connected to said logarithm-compressing means.

2. The image forming apparatus according to claim 1, wherein said temperature sensitive element is electrically connected to said logarithm-compressing means so as to cancel the temperature characteristics of said logarithm-compressing means.

3. The image forming apparatus according to claim 1, wherein said calculating means includes means for calculating a difference between a first output signal generated by said logarithm-compressing means during nondeposition of a developing agent to said image carrier and a second output signal generated by said logarithm-compressing means during deposition of a developing agent to said image carrier.

4. The image forming apparatus according claim 3, wherein said calculating means includes:
A/D converting means for converting said first and second output signals generated by said logarithm-compressing means into first and second digital signals;
holding means for holding said first and second digital signals converted by said A/D converting means; and
calculating means for calculating a difference between said first and second digital signals held by said holding means.

5. The image forming apparatus according to claim 1, wherein said logarithm-compressing means includes a logarithm characteristic element having a temperature dependency.

6. The image forming apparatus according to claim 5, wherein said temperature sensitive element has a temperature dependency opposite to that of said logarithm characteristic element.

7. The image forming apparatus according to claim 6, wherein said temperature sensitive element is thermally coupled with said logarithm characteristic element.

8. An image forming apparatus, comprising:
means for forming an image on an image carrier, said image corresponding to image data to be formed with a developing agent under a predetermined image forming condition;
means for detecting the amount of said developing agent attached to the image carrier, said detecting means comprising:
a) means for directing a light beam toward a surface of the image carrier;
b) means for converting the light reflected from the surface of the image carrier into an electric signal;
c) means for logarithm-compressing the electric signal produced by said converting means, and
d) calculating means for determining the amount of said developing agent by calculating a difference between a first output signal generated by said logarithm-compressing means when said developing agent is not deposited on said image carrier and a second output signal generated by said logarithm-compressing means when the developing agent is deposited on the image carrier;
means for setting said image forming condition in accordance with the amount of the developing agent detected by said detecting means so as to stabilize image density changes of the image formed on said image carrier and
means for compensating for the temperature characteristics of said logarithm-compressing means;
wherein said compensating means includes a temperature sensitive element having an electrical property responsive to the ambient temperature, said compensating means further including a temperature compensating section serving to compensate for the temperature characteristics of said logarithm-compressing means in accordance with an output signal generated by said temperature sensitive element, said temperature sensitive element not being electrically connected to said logarithm-compressing means.

9. The image forming apparatus according to claim 8, wherein said temperature sensitive element is electrically connected to said logarithm-compressing means so as to cancel the temperature characteristics of said logarithm-compressing means.

10. The image forming apparatus according to claim 8, wherein said calculating means includes:
A/D converting means for converting said first and second output signals generated by said logarithm-compressing means into first and second digital signals;
holding means for holding said first and second digital signals converted by said A/D converting means; and
calculating means for calculating a difference between said first and second digital signals held by said holding means.

11. The image forming apparatus according to claim 8, wherein said logarithm-compressing means includes a logarithm characteristic element having a temperature dependency.

12. The image forming apparatus according to claim 11, wherein said temperature sensitive element has a temperature dependency opposite to that of said logarithm characteristic element.

13. The image forming apparatus according to claim 12, wherein said temperature sensitive element is thermally coupled with said logarithm characteristic element.

14. An image forming apparatus, comprising:
means for forming an image on an image carrier, said image corresponding to image data formed with a developing agent under a predetermined image forming condition;
means for detecting the amount of said developing agent attached to the image carrier, said detecting means comprising:
a) means for directing a light beam toward a surface of the image carrier;
b) means for converting the light reflected from the surface of the image carrier into electric signals, said converting means performing conversion to meet the relationship $V=kP$, where V indicates a voltage, k denotes a coefficient and P represents the reflected light and, thus, the voltage V is proportional to the amount P of the reflected light;
c) means for logarithm-compressing the electric signals produced by said converting means; and
d) means for calculating a developing agent deposition amount in accordance with a difference between an output obtained by logarithm conversion of the voltage proportional to the reflected light, said conversion being carried out by said logarithm converting means when said developing agent is deposited on said image carrier, and another output obtained by logarithm conversion of the voltage proportional to the reflected light, said conversion being carried out by said logarithm converting means when said developing agent is not deposited on said image carrier;

means for compensating for the temperature characteristics of said logarithm-compressing means; and means for setting said image forming condition in accordance with the amount of the developing agent detected by said detecting means, so as to stabilize image density changes of the image formed on said image carrier.

15. An image forming apparatus, comprising:

means for forming an image on an image carrier, said image carrier corresponding to image data formed with a developing agent under a predetermined image forming condition;

means for directing a light beam toward a surface of the image carrier;

photoelectric converting means for converting the light reflected from the surface of the image carrier into an electric signal;

A/D converting means for converting said electric signal to a digital signal;

means for logarithm-compressing the digital signal converted by said A/D converting means;

means for calculating the amount of said developing agent attached to the image carrier by said forming means in accordance with a logarithm-compressing output signal output by said logarithm-compressing means; and means for setting said image forming condition of said forming means in accordance with the amount of the developing agent calculated by said calculating means so as to stabilize image density changes of the image formed on said image carrier.

* * * * *